(12) United States Patent
Qiu

(10) Patent No.: US 9,585,601 B2
(45) Date of Patent: Mar. 7, 2017

(54) SYSTEMS, METHODS AND DEVICES FOR DIAGNOSING SLEEP APNEA

(71) Applicant: Chunyuan Qiu, Huntington Beach, CA (US)

(72) Inventor: Chunyuan Qiu, Huntington Beach, CA (US)

(*) Notice: Subject to any disclaimer, the term of this patent is extended or adjusted under 35 U.S.C. 154(b) by 370 days.

(21) Appl. No.: 13/968,191

(22) Filed: Aug. 15, 2013

(65) Prior Publication Data

US 2015/0051449 A1    Feb. 19, 2015

(51) Int. Cl.
*A61B 5/097* (2006.01)
*A61B 5/01* (2006.01)
*A61B 5/085* (2006.01)
*A61B 5/087* (2006.01)
*A61B 5/145* (2006.01)
*A61B 5/0476* (2006.01)
(Continued)

(52) U.S. Cl.
CPC ............ *A61B 5/097* (2013.01); *A61B 5/004* (2013.01); *A61B 5/0086* (2013.01); *A61B 5/015* (2013.01); *A61B 5/0402* (2013.01); *A61B 5/0476* (2013.01); *A61B 5/085* (2013.01); *A61B 5/087* (2013.01); *A61B 5/0826* (2013.01); *A61B 5/0836* (2013.01); *A61B 5/14542* (2013.01); *A61B 5/4818* (2013.01); *A61B 5/6853* (2013.01); *A61B 5/742* (2013.01); *A61B 7/003* (2013.01); *A61B 7/04* (2013.01)

(58) Field of Classification Search
CPC ... A61B 5/0086; A61B 5/0402; A61B 5/0476; A61B 5/0836; A61B 5/087; A61B 5/097; A61B 5/4818; A61B 5/6853; A61B 7/003; A61B 7/04
See application file for complete search history.

(56) References Cited

U.S. PATENT DOCUMENTS 6,142,950 A * 11/2000 Allen .................... A61B 5/087
                                                        600/529
6,183,493 B1 * 2/2001 Zammit .................... A61F 5/08
                                                        606/196
(Continued)

FOREIGN PATENT DOCUMENTS

CA    WO 2013033845 A1 *  3/2013    ............. A61B 7/003
WO    WO 2007137059 A2 * 11/2007    ......... A61B 1/00193

*Primary Examiner* — Gary Jackson
*Assistant Examiner* — Boniface N Nganga
(74) *Attorney, Agent, or Firm* — B. Anna McCoy

(57) ABSTRACT

Systems, methods and devices for diagnosing sleep apnea are provided herein. In one example, a device for detecting airway obstructions may be provided where the device may include a wearable hollow nasal tube to be positioned in an upper airway above a constriction point and an end imaging sensor coupled to the nasal tube to collect airway image data. The device further may include a controller and communication interface to communicatively link and relay airway image data to a select remote device to determine airway obstructions. In some examples, a method may be provided including receiving airway image data from a remote end imaging sensor coupled to a nasal tube disposed within an upper airway above a constriction point, and analyzing the airway image data and displaying in a sleep study report the airway image data to identify airway closures related to obstructive sleep apnea.

21 Claims, 13 Drawing Sheets

(51) Int. Cl.
*A61B 5/0402* (2006.01)
*A61B 5/083* (2006.01)
*A61B 5/00* (2006.01)
*A61B 7/00* (2006.01)
*A61B 7/04* (2006.01)
*A61B 5/08* (2006.01)

(56) References Cited

U.S. PATENT DOCUMENTS

| | | |
|---|---|---|
| 6,216,702 B1 | 4/2001 | Gjersoe |
| 6,440,083 B1 | 8/2002 | Fredberg et al. |
| 6,914,623 B2 | 7/2005 | Ogawa |
| 7,540,843 B2 | 6/2009 | De Backer |
| 8,162,820 B2 | 4/2012 | Moore |
| 8,285,368 B2 | 10/2012 | Chen et al. |
| 2001/0000346 A1 | 4/2001 | Ruton et al. |
| 2005/0065448 A1 | 3/2005 | Stahmann et al. |
| 2005/0245836 A1* | 11/2005 | Star .................. B82Y 10/00 257/253 |
| 2006/0085027 A1* | 4/2006 | Santin .................. A61F 5/08 606/199 |
| 2007/0129603 A1* | 6/2007 | Hirsh .................. A61B 1/00048 600/120 |
| 2010/0121220 A1* | 5/2010 | Nishtala .................. G01N 33/70 600/581 |
| 2010/0240982 A1* | 9/2010 | Westbrook .................. A61B 5/087 600/391 |
| 2011/0155143 A1 | 6/2011 | Shantha |
| 2011/0251457 A1* | 10/2011 | Kezirian .................. A61B 1/0002 600/109 |
| 2012/0022365 A1 | 1/2012 | Mansfield |
| 2013/0012828 A1 | 1/2013 | Aylsworth |
| 2013/0152940 A1* | 6/2013 | Larson .................. A61M 16/0461 128/207.18 |

* cited by examiner

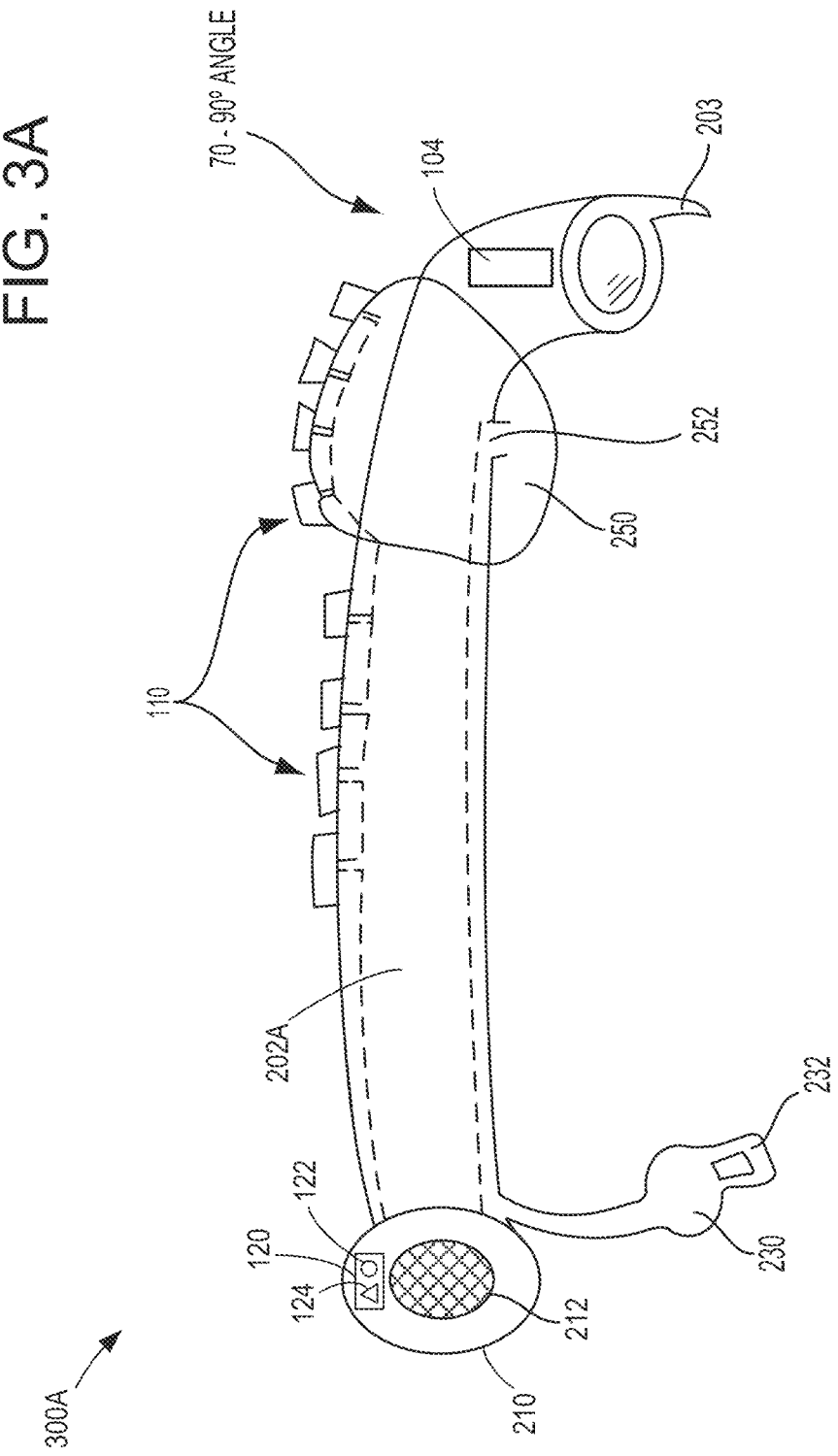

FIG. 6A  AIRWAY OPEN
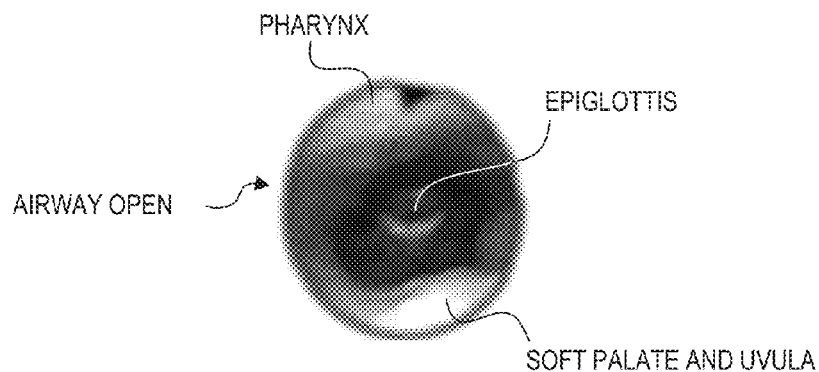
FIG. 6B  AIRWAY PARTIAL OBSTRUCTION
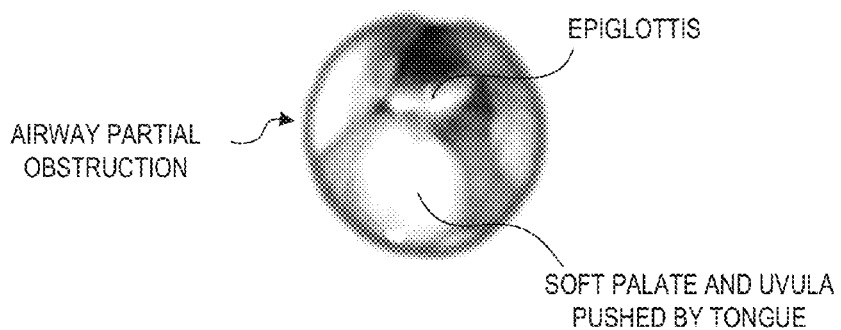
FIG. 6C  AIRWAY OBSTRUCTION
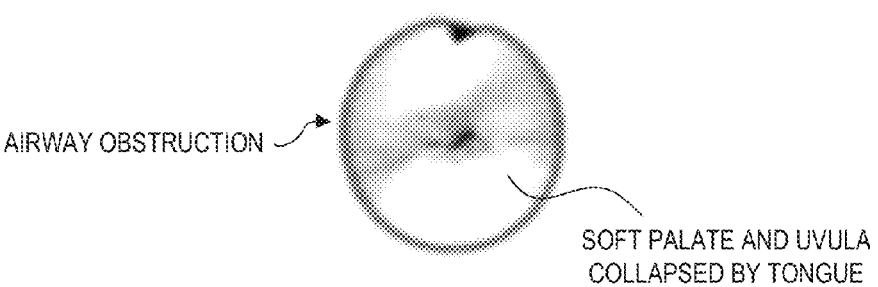
FIG. 6D  PARTIAL RECOVERY FROM AIRWAY OBSTRUCTION
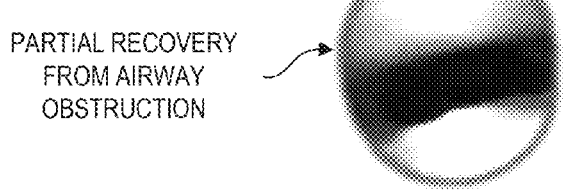

SYSTEMS, METHODS AND DEVICES FOR DIAGNOSING SLEEP APNEA

FIELD

The present description relates generally to systems, methods and devices for diagnosing and monitoring sleep, sleep abnormalities, sleep apnea and related conditions, and more particularly, to systems, methods and devices for observing airway patency during sleep.

BACKGROUND AND SUMMARY

Obstructive sleep apnea (OSA) is a disorder in which a person frequently stops breathing during the sleep cycle as the tongue periodically collapses the upper airway to constrict the flow of air therein. Although the prevalence of OSA in the United States is estimated to be 3-7% in men and 2-5% in women, in some populations (e.g., obese patients with a body mass index greater than 28%) the prevalence increases dramatically. In addition, up to 93% of women and 82% of men having moderate to severe OSA may go undiagnosed for many years if at all due to diagnostic limitations of the currently known methods.

Sleep studies designed to detect and diagnose OSA often occur at a sleep study center using polysomnography (PSG). However, PSG involves hooking a patient up to many wires during the sleep period, which may interfere with the sleep cycle and thereby increase the difficulty of diagnosis. Portable PSG units are known and further designed to reduce PSG complexity but still rely on delayed physiological responses after an airway closure has occurred. Endoscopic techniques are known that are aimed at monitoring breathing and snoring during the sleep cycle. However, such techniques may still require cumbersome equipment to monitor airflows within the upper airway and further lack a means for detecting a sleep position, especially in a remote environment where a trained professional is not present to observe the sleep cycles.

The inventor has recognized disadvantages with the approaches above and herein discloses a wearable hollow nasal tube to be positioned in an upper airway above a constriction point that comprises an end imaging sensor coupled to the nasal tube to collect airway image data; and a controller and communication interface to communicatively link and relay the airway image data during sleep to a select remote device to determine airway obstructions. In one embodiment, the device further comprises an inflatable balloon to anchor the nasal tube such that the end imaging sensor, which is placed at a distal end of the nasal tube, is disposed in an airway image data collection position. Thereby, the device may be positioned within a nasopharnyx above the constriction point with the end imaging sensor angled downward relative to a nose opening, which allows for enhanced viewing of the airway. As described herein, the device may further include one or more biophysical sensors for the enhanced detection of airway patency during OSA screening and diagnosis while an air sampling port configured for monitoring airflow and performing air analysis (e.g., capnography) while visual images of the upper airway are collected may also be included. The device may advantageously further include a head positioning sensor for detecting a device orientation relative to a head position, which allows airway patency to be correlated to sleep positions during sleep studies. Therefore, by placing the nasal tube and end imaging sensor above the point of airway constrictions, breathing patterns can be monitored during sleep without interfering with sleep cycles while the device records and communicates with a remote computing device connected via a network connection. In this way, the device and methods described can be used to advantage for diagnosing OSA by directly imaging the airway, particularly in response to a sleep position, and especially when sleep activities occur remotely.

As provided herein, in some examples, sleep studies using the disclosed device and systems thereof may be performed in a first location while one or more breathing patterns are remotely analyzed in a second location simultaneously or subsequently, which allows for real-time or early diagnosis of sleep abnormalities in a more convenient manner for both the patient and healthcare professional. For example, a patient may perform the sleep study in the comfort of their own home at night in the U.S. while observations are made and results of the sleep study are analyzed during the day in China (or other locations), or vice versa. Furthermore, in some embodiments, the device may include a clock or timing device, which allows recorded measurements to be time-stamped and thereby synchronized for further data analysis of sleep patterns.

The above advantages and other advantages, and features of the present description will be readily apparent from the following Detailed Description when taken alone or in connection with the accompanying drawings. It should be understood that the summary above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

BRIEF DESCRIPTION OF THE DRAWINGS

The advantages described herein will be more fully understood by reading an example of an embodiment, referred to herein as the Detailed Description, when taken alone or with reference to the drawings, where:

FIGS. 6A-D show example schematic illustrations of an airway closure and measurement;

DETAILED DESCRIPTION

Figure 1A:
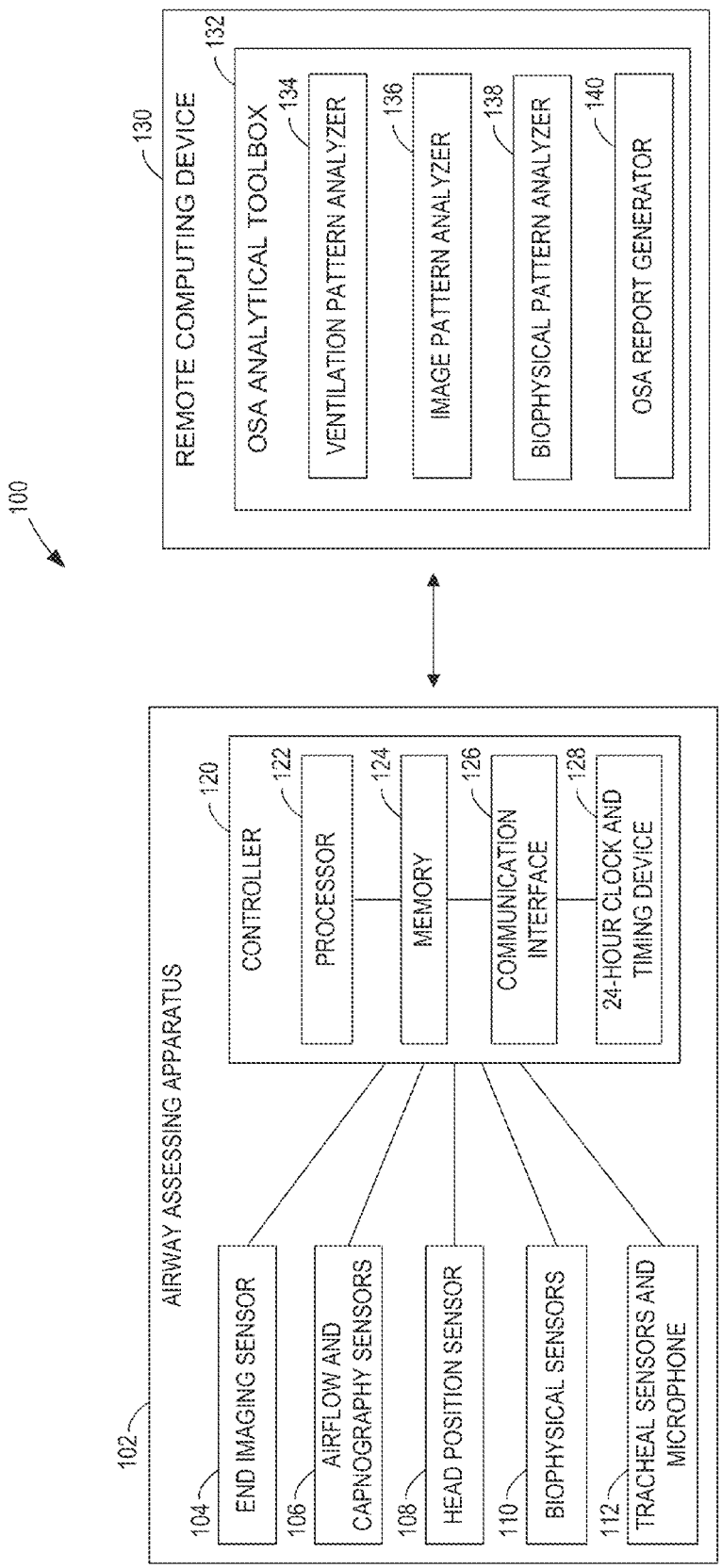
FIG. 1A shows an exemplary schematic diagram of the system according to the present disclosure.

A wearable tubular airway assessing apparatus and methods for determining airway constriction are described that allow visual images of the constriction to be collected in combination with sensed airway and head position data. In one example, the device may be configured for sending and receiving data signals, which thereby allows for real-time data transmission and remote control of the device while a sleep study is performed in one location and the data analyzed in a second remote location. Inclusion of a head positioning sensor further allows airway patency to be correlated with sleep positions during the sleep study for enhanced OSA diagnosis. Although the device is described in some embodiments including one or more other sensors (e.g., airflow and/or capnography sensor) that operate in combination with the end image sensor described, it is to be understood that in some embodiments, the device may comprise the wearable hollow nasal tube with an end imaging sensor to collect airway image data while one or more other sensors may be a peripheral device (e.g., a commercially available pulse oxymeter) whose operation may be coordinated and/or synced with the airway assessing apparatus herein. Therefore, the airway assessing apparatus of the present disclosure allows imaging of the upper airway during sleep in combination with collection of other sleep physiological data for diagnosing obstructive sleep apnea (OSA). As described herein, in some embodiments, the airway assessing apparatus may comprise a nasopharyngeal imaging sensor and light source, a head position sensor, an information processing center and control system, and various sensors, such as an airflow sensor, oxygen and/or carbon dioxide sensors (e.g., capnography), an electroencephalography (EEG) sensor, electrocardiography sensor (EKG), and one or more sound-detecting devices, etc. In particular, the nasal imaging sensor of the airway assessing apparatus may be positioned within the nasal cavity above the oropharynx to allow visual confirmation of airway patency or obstruction from a collapsed tongue and uvula in OSA.

The device described is further configured for secure placement within the nasal cavity for long periods of time. For instance, during a sleep study a user may wear the tubular apparatus for up to 12 hours while data is collected in the manner described below. Therefore, the wireless device is also designed for mobility and allows the patient a simple means to attend to the infrequent breaks that sometimes occur during the sleep cycle (e.g., using the restroom, getting a drink of water, etc.). As such, the device may be easily inserted into the cavity as a wearable apparatus that maintains a substantially constant view of the airway region throughout the entirety of the sleep study.

As a further example, the device may be positioned within the nasal cavity during the awake state to record baseline measurements of airway diameter and other physiological parameters. Then, the same parameters may be subsequently recorded during the sleep state at a later time, which thereby allows for determination of one or more facts, including, but not limited to, the occurrence, frequency, and degree of airway obstruction or OSA. In addition, inclusion of a head position sensor, in some embodiments, may enable a device orientation relative to a head position to be determined during the sleep cycle. In this way, the device can record visual images of the airway diameter changes or obstruction in relationship to body posture or head position. For purposes of clarity, the same reference numbers are used in the drawings herein to identify similar elements.

FIG. 1 shows an exemplary schematic diagram of OSA diagnostic system 100 according to the present disclosure. As described in detail below, airway assessing apparatus 102 may include various sensors for visualizing and detecting ventilation patterns associated with airway obstruction. For example, in the embodiment herein described, end imaging sensor 104 may be a thermal or regular camera located at the distal end of a tube within airway assessing apparatus 102 that is used to visualize the upper airway from above the point of airway constriction. It should be appreciated that the end imaging sensor may be positioned at the end of the tube in some embodiments, substantially near the end of the tube in other embodiments or any other position that enables visualization of the upper airway from above the point of airway constriction. Nasal imaging sensor 104 further allows for collection of continuous or intermittent video (e.g., 1 frame/second) and thereby records the respiratory dynamic, airway patency and anatomic changes within the upper airway during the cycles of sleep. In particular, the images can be used to determine the degree and duration of upper airway obstruction relative to the baseline profile collected when the subject is awake. For example, imaging data may be used to identify the frequency and duration of airway narrowing (e.g., hypopnea is diagnosed if a partial obstruction occurs for more than 10 second) or collapse (e.g., apnea is diagnosed if a substantially complete obstruction occurs for more than 10 second) which may be determined or calculated from the images collected. In this manner, an Apnea-hypopnea Index (AHI) can be further generated as one of the diagnostic indicators of OSA. AHI refers to the number of apnea and hypopnea episodes occurring within a time period, for instance, per hour of sleep. Although traditional diagnosis of OSA using AHI routinely relies upon secondary substantial indicators of complete or incomplete airway obstruction, in contrast, the device and system described herein obtains the AHI using direct imaging of the airway. Further, as also described herein, a light source (e.g., an LED bulb) may also be included for illuminating the upper airway to enhance the viewing environment within the internal cavity. However, in embodiments where the end imaging sensor is a thermal imaging sensor, the light source may be optionally included.

In some examples, airway assessing apparatus 102 may include insertion tubes. For example, in the embodiment illustrated, and not as a limitation, two tubes may be provided for inserting into the nasal and/or oral cavities. In some examples, the tubes may be communicatively linked with one or more airflow speed and capnography sensors 106, also referred to as airflow sensors. These sensors may be included within the device for measuring or indicating an airflow, gas level and/or exchange rate during the sleep cycle or some other period. Inclusion of one or more airflow sensors further allows correlation to the visual images for differentiating OSA from normal reflex responses (e.g., unintentional swallowing, sneezing and/or coughing) during sleep. As described herein, one or more airflow sensors can be incorporated into the device that allow airflow or $CO_2$ measurements through the nose, mouth and/or trachea either separately or simultaneously.

In some instances, occurrence of an airway constriction may depend on a particular sleep position adopted during the sleep cycle. Therefore, in one example device, a head position sensor 108 may be embedded therein for indicating an orientation of the device relative to a patient head position. For example, head position sensor 108 may be an accelerometer capable of measuring a local inertial frame relative to the gravitational field. As such, placement of the airway assessing apparatus into one or more cavities relative to a head position may allow the position of the device relative to the gravitational field to be determined. The head position data may be used to determine or extract a patient sleep position (e.g., lying down in the supine position with face up) throughout the sleep cycle. The patient sleep position data may be further synchronized and correlated with other sensor and airway blockage data. As a result AHI can be established for various sleep positions, e.g., supine position, left lateral position or right lateral position. Furthermore, a head movement counter to collect head position data including a number or frequency of head movements during sleep may also be established in order to determine the quality of sleep.

In some embodiments, various additional biophysical sensors 110 for detecting EEG (electroencephalography), EKG (electrocardiography), EOG (electrooculography), EMG (electromyography) and/or tissue oxygen saturation may also be communicatively linked with the device. Therefore, in one example, the device may include an oxygen saturation sensor to collect airway data, where the airway data is relayed to a select remote device along with the airway image data. With respect to sensor placement, the biophysical sensors may be positioned on a surface of the device (and/or within the device) or on a related accessory or component. Inclusion of biophysical sensors may enable select autonomic reflex data to be collected and correlated to the visual images for confirmation of the OSA diagnosis. In a further example embodiment, airway assessing apparatus 102 may also include one or more trachea sensors 112 for monitoring various conditions simultaneously from above and below the point of constriction. For example, trachea sensor 112 may be a sound-detecting device such as a microphone, stethoscope or Doppler sound device.

In another example embodiment, trachea sensor 112 may be an oxygen sensor or a nitrogen sensor for monitoring oxygen and/or nitrogen levels that exist naturally in the trachea. In yet another example, the trachea sensor may be a magnetic sensor such as a permanent magnet or electromagnet that is configured to generate a magnetic field within the trachea. As a non-limiting example, trachea sensors 112 and air sampling tube 220 (shown in FIGS. 2 and 3), which may be disposed at any location on the device, may be included to sample the air and airflow within the nasal and/or oral cavity. Use of the trachea sensor and air-sampling tube may provide additional gas analysis, for example, via capnography or mass spectrometry, etc.

Referring back to FIG. 1, controller 120 may include processor 122, memory unit 124, and a communication interface 126. Processor 122 and communication interface 126 may be linked by a bus to memory 124. Controller 120 may also be configured to communicate with remote computing device 130 via communication interface 126. In some embodiments, memory 124 may include both non-volatile and volatile memory, and programs or algorithms may be stored in non-volatile memory and executed by the processor using portions of volatile memory to accomplish the operations described herein. Controller 120 may also include a programmable 24-hour clock and timer device, which allows synchronization of data collection processes and, in some embodiments, may further enable the collected data to be time stamped for future analysis.

Airway assessing apparatus 102 may be configured to communicate with a remote computing device 130. As such, controller 120 may further include a transmitter for sending and receiving wireless signals. For example, data stored locally within the device may be uploaded to a remote computing device 130 through one or more network connections (e.g., via the internet through a WiFi connection) for review by a trained professional at a provider's or doctor's office and/or sleep study center. Thereby, the device according to the present disclosure may enable, in some embodiments, data to be uploaded remotely in real-time or at the end of the study. Alternatively, or additionally, a port, such as a data input/output port, may be included for directly connecting the device to a remote computing device (e.g., a computer in a doctor's office or other user device), which may allow stored data to be downloaded directly to the computing device at the end of a study.

In some examples, remotely recorded data stored within memory unit 124 may be viewed manually by one or more trained professionals and/or automatically analyzed by a data processor. For instance, OSA analytical toolbox 132 may be present on remote computing device 130 for analyzing one or more sensed data patterns in order to diagnose obstructive sleep apnea or degree of airway constriction during the sleep cycle. For simplicity, analytical toolbox 132 is shown comprising a ventilation pattern analyzer 134 for analyzing and comparing one or more data patterns associated with obstructive sleep apnea; image pattern analyzer 136 for assessing an obstruction or degree of obstruction while also differentiating the closure from other reflex actions that occur within the upper airway; biophysical pattern analyzer 138 for analyzing one or more biophysical data patterns; and an OSA report generator 140 for generating a formatted printout of diagnostic results to facilitate physician diagnosis.

Although OSA analytical toolbox 132 is shown including pattern analyzer 134, image pattern analyzer 136, biophysical pattern analyzer 138, and report generator 140, these tools are shown for example and are non-limiting. Other analytical routines are also possible. As an illustration, analytical toolbox 132 may comprise tools for diagnosing OSA based on collected data. For example, one or more of the tools therein may be used to calculate AHI, or the Apnea-Hypopnea index, which refers to the number of episodes of apnea and hypopnea occurring per hour. As noted above, Hypopnea occurs when a partial obstruction lasts for 10 seconds or longer whereas Apnea occurs when a substantially complete obstruction lasts for more than 10 seconds. Moreover, the AHI scale may be used to diagnose OSA based on the number of episodes detected. As one example, mild OSA is diagnosed upon detecting 5-15 episodes per hour; moderate OSA is diagnosed upon detecting 15-30 episodes per hour; and severe OSA is diagnosed upon detecting over 30 episodes per hour. Additionally or alternatively, such data may be combined with information from other sensors to arrive at an OSA diagnosis. For instance, head movement or position data collected by head position sensor 108 may be used in combination with images of the airway to further determine sleep quality. As another example, a decreased saturation of peripheral oxygen ($SPO_2$), or oxygen saturation may also be measured (e.g., by pulse oximetry) along with EEG or EKG changes and correlated to one or more of a data pattern or sleep position. In this way, the device described may be used for diagnosing OSA when determining sleep quality.

Figure 1C:
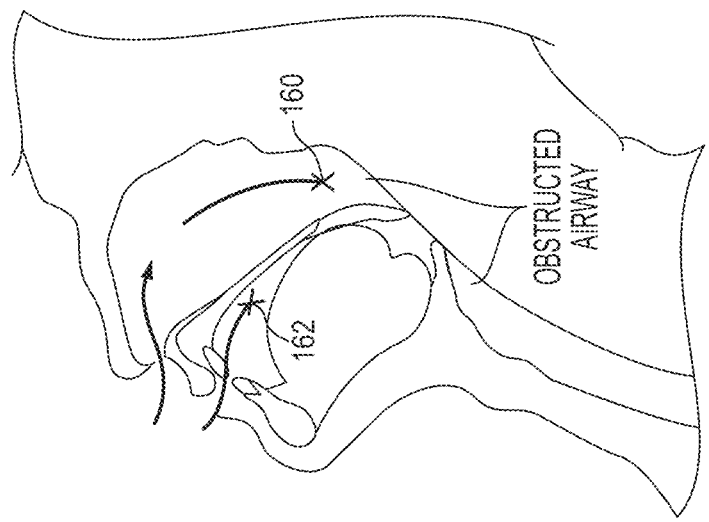
FIGS. 1B-D show example airways to illustrate normal inhalation during sleep and obstructed airways that represent complete and partial airway blockages.
Figure 1B:
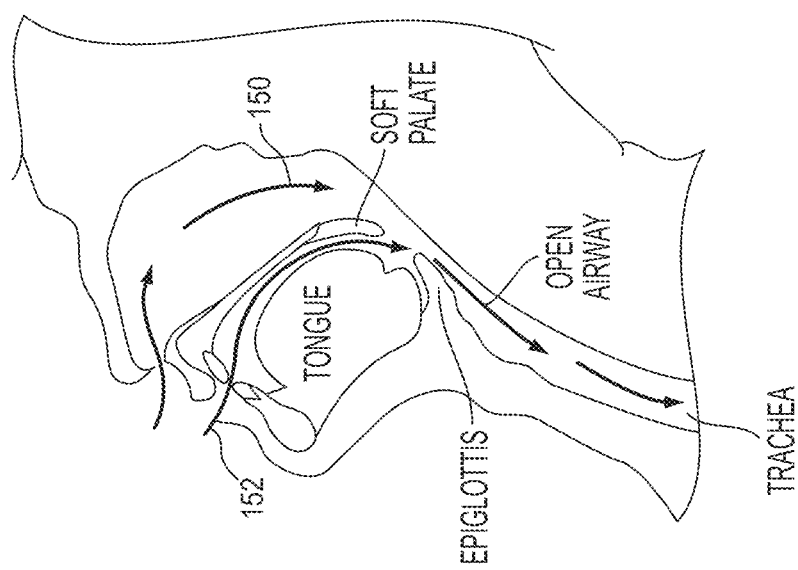

FIGS. 1B and 1C show example airways to illustrate how a blocked passage may occur due to tongue collapse during the sleep cycle. As illustrated, the figures show an example inhalation pattern of an open airway and an obstructed airway along with various anatomical features for reference.

For example, FIG. 1B shows that during normal inhalation, nasal airflow 150 and oral airflow 152 enter the nasal and oral cavities, respectively. Then, because the airway is open and therefore not blocked by a collapsed tongue, the two airflows may converge into a single airflow that is further directed into the trachea and to the lungs (not shown) of an individual. Conversely, FIG. 1C shows that the airway becomes obstructed when the tongue collapses to push the soft palate (including the uvula) and epiglottis toward the back of the airway. In response to the obstruction event, the nasal and oral airflows may be blocked as indicated by the X-capped lines shown at 160 and 162, respectively.

Figure 1D:
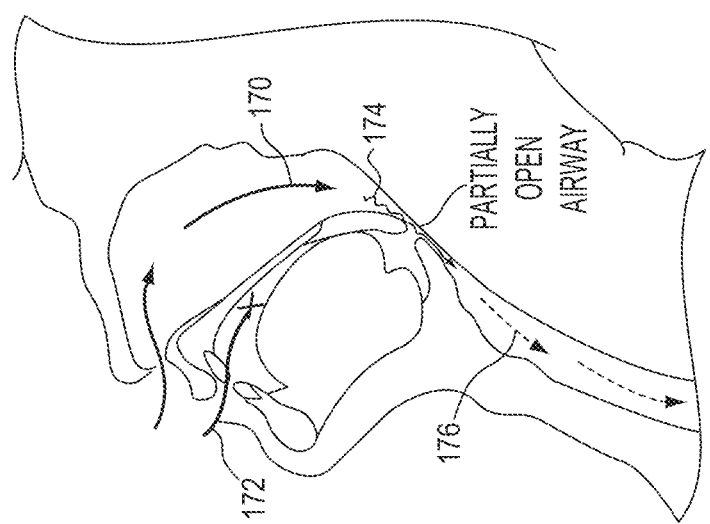

For clarity, FIG. 1D shows a partially obstructed airway wherein airflow turbulence occurs at the point of constriction. As shown, in one example, nasal airflow 170 may occur while oral airflow 172 is simultaneously blocked. However, other examples relative airflow configurations are possible. Therefore, both airflows may also be partially open or, alternatively, air may flow through the oral cavity while airflow through the nasal cavity is simultaneously blocked in some instances. Because the airway is partially obstructed, a turbulent airflow 174 may occur wherein the airflow through the point of constriction is chaotic and irregular. In some instances, turbulent airflow 174 may result in the unpleasant sounds of snoring as vibrations within the respiratory structures occur that are due to air movement through the partially obstructed airway during breathing while sleeping. As a result, in some instances, airflow 176 may be reduced compared to nasal airflow 170 as shown by the dashed lines therein. In this manner, one or more airways may become blocked that are detectable using the methods according to the present disclosure.

Figure 2A:
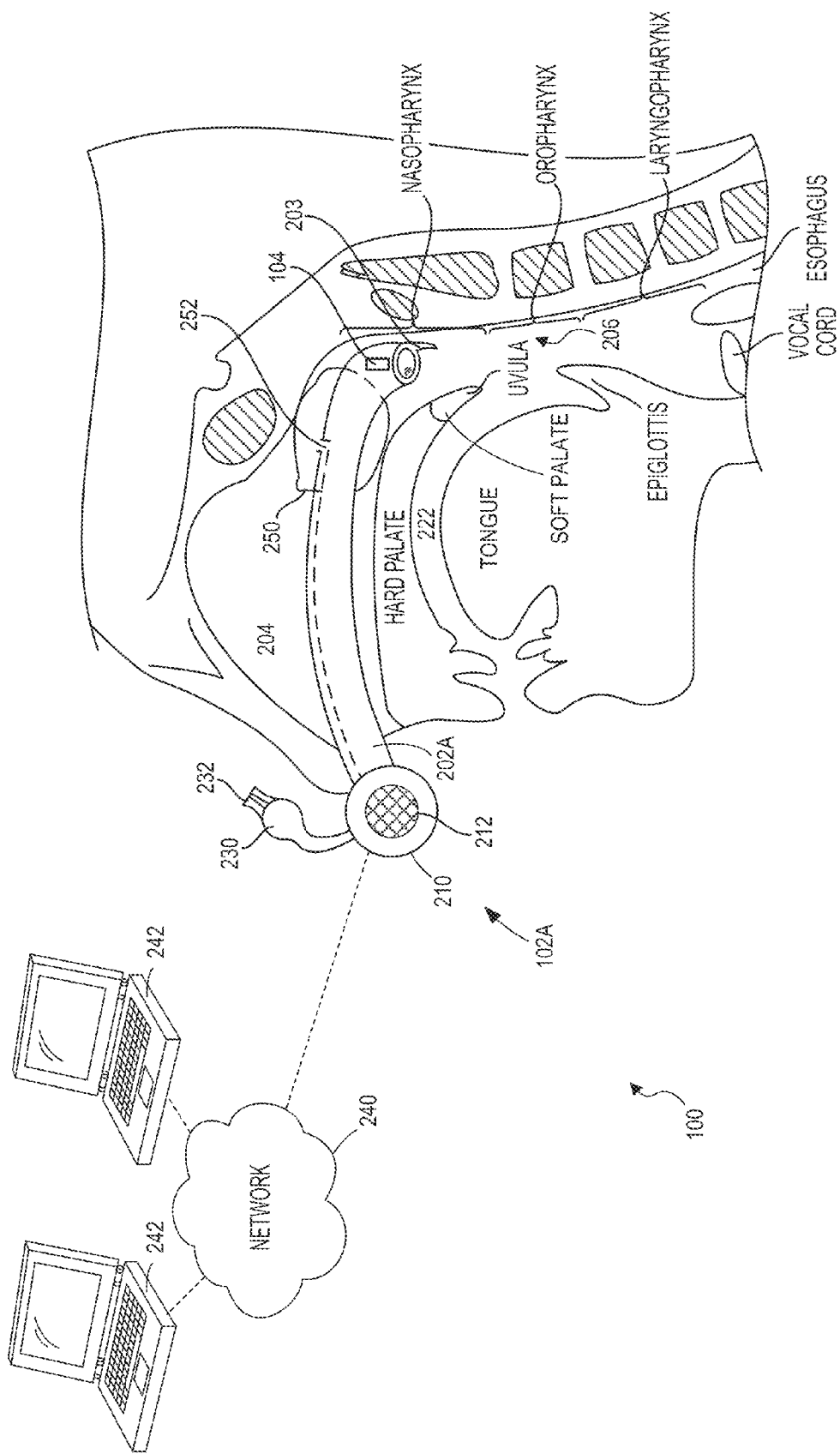
FIGS. 2A and B show example embodiments of the system of FIG. 1A with the airway assessing apparatus inserted into the nasal cavity.
Figure 2B:
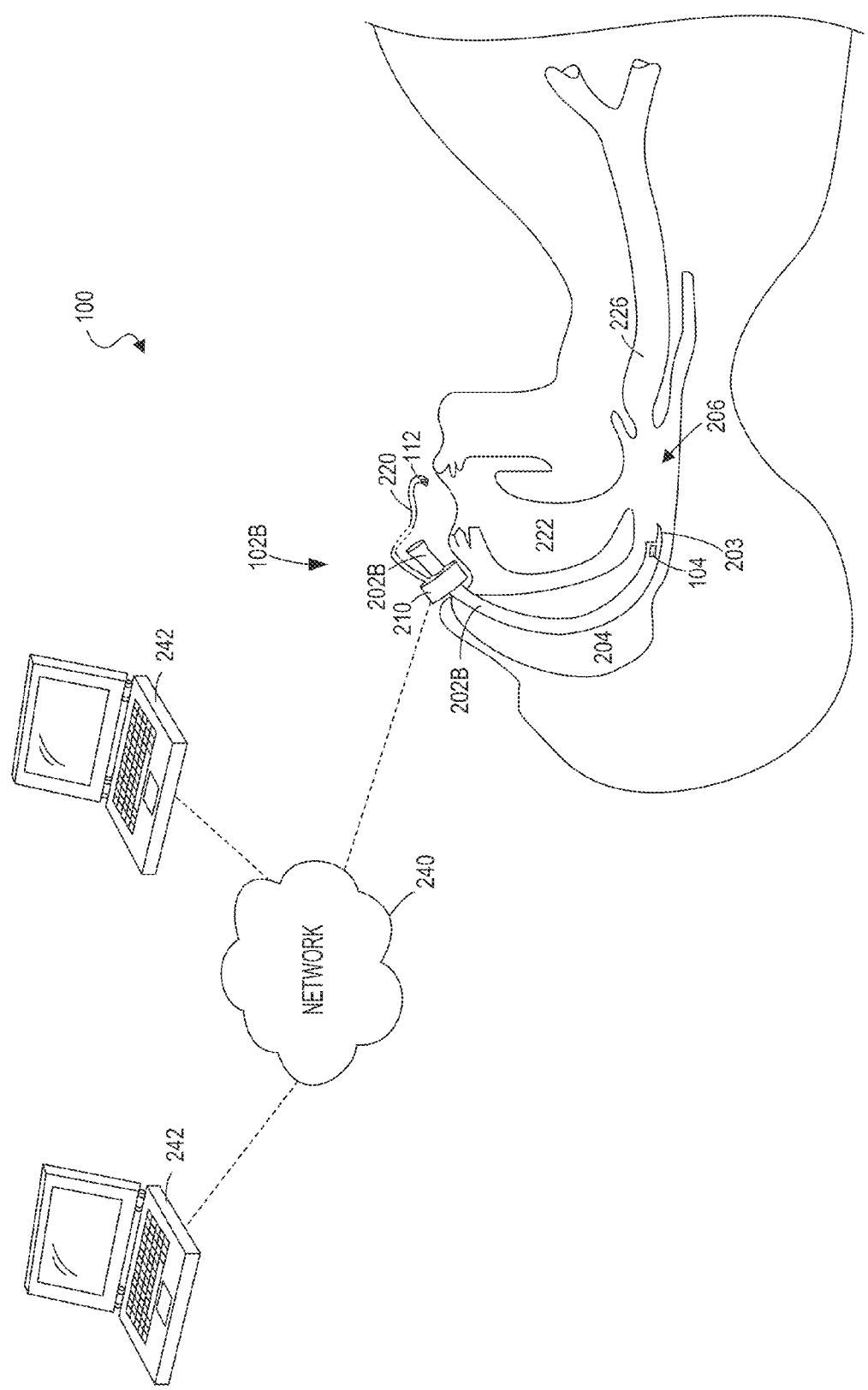

FIGS. 2A and 2B show example embodiments of OSA diagnostic system 100 in accordance with the present disclosure. For example, FIG. 2A shows airway assessing apparatus 102A with nasal tube 202A inserted into nasal cavity 204. Nasal tube 202A may be a flexible hollow tube adapted for insertion into the nasal cavity. In some examples, nasal tube 202A may include a soft, bendable beak-like tip 203 or other configuration that allows for downward deflection and easier insertion and placement of the device within the cavity above constriction point 206. In the first embodiment shown, airway assessing apparatus 102A includes nose stopper 210 along with mesh 212 that enables air to pass through the hollow device and into the airway. The device may also include pilot balloon 230 with air injection port 232 (or valve) that is used for inflating balloon 250 through inflation opening 252. In the embodiment shown, inflatable balloon 250 may be included along with the nose stopper to anchor the device in place during the sleep study period. In this way, inflating the balloon allows for increased contact between the balloon and nasal cavity, which thereby acts to anchor the device and prevent inward or outward movement of the device during the sleep study. Therefore, placement of the device is stabilized, which allows for a more consistent imaging environment and enhanced clinical utility according to the methods described herein. Moreover, the seal between balloon 250, which may be one or more balloons in some embodiments, and the nasal cavity may further create a tunnel through the hollow device that acts to direct the airflow there through. As such, airflow through the device is optimized to enable more sensitive diagnostic measurements during the sleep study.

In the example illustrated, nasal tube 202A is a tube with 70 to 90 degree bend at the distal end for viewing the airway when placed above constriction point 206. As such, the tube shape shown, which is non-limiting, allows for an enhanced view of the uvula, soft palate, and airway constriction via end imaging sensor 104. Herein, end imaging sensor 104 is a camera for simplicity. However, in other embodiments, end imaging sensor may be a thermal imaging device. Therefore, end imaging sensor 104 is a camera located at the distal end of nasal tube 202A. Although the embodiments herein describe a curved device or a device with a bend for enhanced viewing of an airway constriction, it has been contemplated that end imaging sensor 104 may further include components for adjusting a position relative to the nasal tube. However, for simplicity, end imaging sensor 104 is herein described with an orientation giving a clear view of constriction point 206 when placed into the nasopharynx as shown. For instance, when the distal end of nasal tube 202A is positioned within the nasopharynx as shown in FIG. 2A, the tube end forms an angle ranging from 70 to 90 degrees with respect to nose stopper 210. Therefore, the end imaging sensor is angled downward relative to a nose opening to view an airway, and the angle of placement is generally described as being near, but less than 90 degrees for simplicity, which allows for optimal viewing of the airway and any constrictions occurring therein.

FIG. 2B shows a second embodiment of airway assessing apparatus 102B that also includes nasal tube 202B with a soft, bendable end and a flexible beak-like tip 203 for easier insertion and downward deflection to increase the ease of placement within nasal cavity 204 above constriction point 206. In one embodiment, beak-like tip 203 is integrated into the bendable nasal tube and comprises a piece of plastic having the contour of a beak. Thereby, the beak-like tip and nasal tube may form a single, continuous structure. However, this is non-limiting and in other embodiments, the beak-like tip, which is soft and flexible, may also comprise a separate tip configured for addition to the end of the nasal tube and/or may be made of other materials (e.g., rubber) so long as the material is insertable into the body for long periods of time. As noted above, the tip allows for easier and nontraumatic insertion of the tubular airway assessing apparatus into the nasal cavity, since traumatic insertion (and bleeding) may interfere with sensor operation, and in some instances compromise image sensor clarity. For example, during insertion into the nasal cavity, the tip may contact the back of the cavity just above the nasopharynx. In response, the beak-like tip may flex and slide down the nasal cavity to create the downward deflection that advantageously places end imaging sensor 104 above airway constriction 206. In addition, nasal tube 202B, is a hollow tube with a diameter smaller than a nostril opening and length (e.g., less than the distance between the nose and ear) that allows placement within the nasal cavity above the point of constriction (e.g., within the nasopharynx before the oropharynx). As provided in this example, the device may allow for spontaneous nose breathing while not interrupting the sleep cycle. As further shown, nasal tube 202B is connected to nose stopper 210, which divides nasal tube 202B into first and second portions and is included to prevent the device from being inserted too far into the nasal cavity, which may compromise the diagnostic process by allowing the tube to bypass the constriction point and thereby to become a treatment device. Therefore, nose stopper 210 stabilizes the position of the device relative to the nasal cavity and thereby offers a consistent environment for viewing the airway passage, especially over long periods of time (e.g., 4-10 hours) associated with a sleep duration. In some embodiments, air sampling tube 220 that may be positioned in front of the mouth 222 may be coupled to nasal tube 202B and nose stopper 210. However, this is non-limiting and the tube may be connected at other locations along nasal tube 202B.

Air sampling tube 220 is used to indicate mouth breathing. In one example embodiment, air sampling tube 220 may include a microphone or other audio device. In some examples, the microphone may be positioned in front of the neck to indicate airflows. As such, in some instances, the length of air sampling tube 220 may be substantially long so as to reach the neck region during a sleep study. However, the length of air sampling tube 220 is non-limiting, and in other examples, the air sampling tube may be an air sampling port for gas analysis, where airflow is sampled at a constant rate for capnography analysis (e.g., a closed tube sticking out from air sampling tube 220). Inclusion of the air sampling tube 220 allows false positive results to be substantially eliminated since some people are total mouth breathers that exhibit no airflow through the nasal cavity. For these people, airflow from the mouth or microphone may indicate breathing whereas the images collected may show an airway collapse, which indicates a false positive result that is not considered as an episode of apnea. Moreover, false negatives may occur when no flow is detected via the mouth, nose and trachea microphone, but where images show an open airway, for example, as occurs in central sleep apnea, which is a brain condition that occurs due to an instability of the body's feedback mechanism to generate neural respiration signals.

In FIGS. 2A and 2B each airway assessing apparatus is connected to network 240. As such, the portable device may be configured to connect to network 240 while enabling communications with a plurality of remote computing devices 242, which may be configured to automatically analyze data received therefrom. Computing device 242 may be located remotely to a location where a sleep study is performed. Connections between each airway assessing apparatus and computing device 242 therefore allows for monitoring and controlling the device remotely. For example, information from end imaging sensor 104 (e.g., visual images) may be sent to computing device 242 during a sleep study. In turn, a user may also receive instructions from network 240. In this way, the sleep study may be monitored, controlled and/or supervised remotely. Communications between the airway assessing apparatus and network may be useful when the device is used in a sleep study center or home environment, or when the study is performed by less-trained personnel. As such, the sleep study may be performed at one location and supervised by a person using computing device 242 at the same location. Or, a user may use computing device 242 to remotely operate and control the airway assessing apparatus disclosed. For example, data collection may be initiated by a doctor in one location while the study is performed at another location. Furthermore, the airway assessing apparatus and a computing device may be connected via a network through a wire or wireless connections.

Figure 3B:
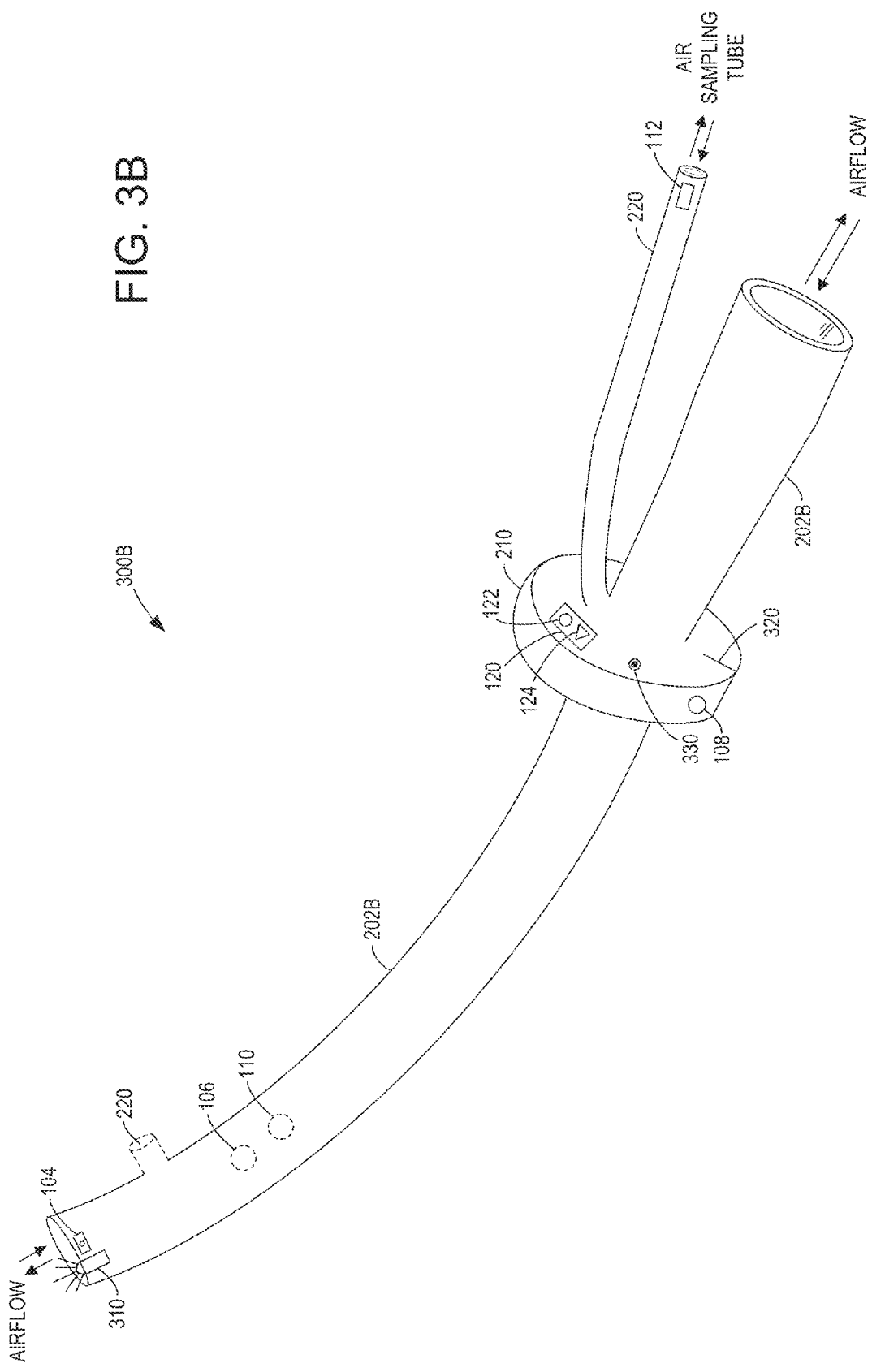
FIGS. 3A and B show exemplary hollow nasal imaging devices according to the present disclosure.

FIGS. 3A and 3B show exemplary hollow nasal imaging devices according to the present disclosure. In FIG. 3A, airway assessing apparatus 102A that is described with respect to FIG. 2A is shown in more detail. As noted already, airway assessing apparatus 102A is a first embodiment of hollow nasopharyngeal imaging device 300A. As described already, airway assessing apparatus 102A includes hollow nasal tube 202A that is shown with a 70 to 90 degree bend at the distal end of the flexible tubing. Thereby, the shape of the device allows for enhanced views of the airway upon placement into the nasal cavity. Beak-like tip 203 is also included and further allows for easier placement of the device within the nasopharynx in the manner already described. End imaging sensor 104 is located at the distal end such that images may be collected of the airway during a sleep study. Nasal tube 202A is further connected to nose stopper 210, which is included to prevent the device from being inserted too far into the nasal cavity. Therefore, nose stopper 210 stabilizes the position of the device relative to the nasal cavity and thereby offers a consistent environment for viewing the airway passage, especially over long periods of time (e.g., 4-10 hours) associated with a sleep duration. In the embodiment shown, nose stopper 210 includes mesh 212 that allows for an airflow therethrough.

As described above, airway assessing apparatus 102A also includes pilot balloon 230 with air injection port 232 (e.g., a valve) that is used for inflating balloon 250 through inflation opening 252. In the embodiment shown, balloon 250 may be included to anchor the device in place along with the nose stopper during the sleep study period. For example, the balloon may be inflated to allow for increased contact between the balloon and nasal cavity, which thereby acts to anchor the device and prevent inward or outward movement of the device during the sleep study. In this way, the inflatable balloon is included to anchor the nasal tube such that the end imaging sensor is disposed in an airway image data collection position. As such, placement of the device is stabilized, which allows for a more consistent imaging environment and enhanced clinical utility according to the methods described herein. Moreover, the seal between balloon 250, which may be one or more balloons in some embodiments, and the nasal cavity may further create a tunnel through the hollow device that acts to direct the airflow therethrough. Therefore, airflow through the device is optimized to enable more sensitive diagnostic measurements during the sleep study. In addition, balloon 250, may be used to adjust the position of one or more sensors through balloon deployment. Thereby, as described in more detail below, a sensor position may be adjusted by inflating a balloon located beneath the sensor in response to an output below a threshold in order to adjust the relative height of one or more sensors and thereby increase the surface contact area between the sensor and a wall of the nasal cavity. Dashed lines are included to indicate a surface within the hollow tube wherein air from injection port 232 can pass through to reach one or more balloons within the device.

With respect to the structure of airway assessing apparatus 102B, FIG. 3B shows an exemplary hollow nasopharyngeal imaging device 300B according to the second embodiment of the present disclosure. Hollow nasopharyngeal imaging device 300 includes nasal tube 202B connected to nose stopper 210 and further coupled to second air sampling tube 220. Upon placement of the device into a cavity, bi-directional airflow may occur. For example, during exhalation when no airway closure occurs, air may flow from trachea 226 into the nasal cavity and through nasal tube 202B. Additionally, or alternatively, air may also flow from trachea 226 into the oral cavity and through mouth 222. In the same manner, during inhalation external air may be conducted into the body by entering the proximal end of nasal tube 202B and further branching into two airflows that travel through nasal tube 202B and second air sampling tube 220, which in some instances may be a closed port coupled to the airflow through airway assessing apparatus 102B as indicated by the dashed air sampling tube 220 in FIG. 3B, and wherein airflow may be sampled at a constant rate for capnography analysis. Alternatively, when an airway is constricted, one or more of the airflows through the device may be reduced or substantially eliminated. Although the description herein places a nasal tube into the nasal cavity and the second air sampling tube in front of the oral cavity, in some embodiments, one or the other of the two tubes may be placed alternatively to record data using one or more other data sensors. For example, air sampling tube 220 may alternatively include a microphone sensor that is placed in front of the trachea to monitor an airflow therethrough. Further still, in other examples, a device may include a single tube for visually monitoring an airway from above a point of constriction.

Returning again to FIG. 3B, in the example illustrated, nasal tube 202B is a tube that is curved relative to the longitudinal axis of the device to enable placement of the device relative to constriction point 206. As such, tube curvature allows an enhanced view of the uvula and soft palate in addition to airway constriction via end imaging sensor 104, which in one embodiment is a camera located at the distal end of nasal tube 202B. Although the device is described as being curved relative to the longitudinal axis, the amount of curvature may vary during operation. For instance, when the distal end of nasal tube 202B is positioned within the nasopharynx as shown in FIG. 2B, the tube end forms an angle ranging from 70 to 90 degrees with respect to nose stopper 210. Therefore, the angle of placement is generally described as being near, but less than 90 degrees for simplicity, which allows for optimal viewing of the airway and any constrictions occurring therein.

As noted above, in some embodiments, the device may further include nasopharyngeal light source 310 near end imaging sensor 104 that allows for illuminating the upper airway and increased viewing capabilities therein. As one example, nasopharyngeal light source 310 may be an intermittent flash light or a constant LED light with a small area (e.g., less than 1 mm$^2$) having low energy consumption and high durability to accommodate the nature of a lengthy sleep study. However, in other embodiments, nasopharyngeal light source 310 may be a thermographic or infrared camera for forming an image using heat profiles within the airway.

End imaging sensor 104 may be configured for continuous or intermittent video (e.g., 1 frame/second) recording during sleep cycles. As such, dynamic images of the anatomic changes of the upper airway can be viewed to assess an obstruction or degree of obstruction compared to a baseline profile collected when the subject is awake. Because each image recording is time stamped, the frequency and duration of airway narrowing or collapse may also be calculated from the images collected. For example, imaging data may be used to determine the airway opening is 50% narrowed for 10 seconds or more at a frequency of 20 times per hour, which is further used to calculate an AHI consistent with moderate OSA. Alternatively, as another example, imaging data may be used to determine the airway is 100% obstructed for 10 seconds or more with a frequency of 30 times per hour, which produces an AHI consistent with severe OSA. Therefore, according to the present disclosure, the airway assessing apparatus described may allow AHI calculation from direct imaging of the airway.

Airflow speed and composition sensors shown schematically at 106 may also be included within the device. Inclusion of airflow sensors allows for the airflow through the nose, mouth and/or trachea to be monitored separately or simultaneously in some instances. An airflow indicator may determine airflow from the mouth to generate airflow data. Thereby, data from one or more airflow sensors may provide confirmation of the visual images collected and further allow differentiation of OSA from normal physiological reflexes that occur (e.g., swallowing, sneezing, and coughing during sleep). For example, during airway obstruction, the airflow through both the nasal cavity and oral cavity (or trachea) may cease whereas during a reflex response, air may continue to flow through the oral cavity and trachea. Alternatively or additionally, in some instances, airflow sensor 106 may be one or more of an $O_2$ or $CO_2$ sensor (e.g., capnography) for determining a gas level or exchange rate within an airway based on the data collected.

Biophysical sensors are schematically depicted at 110 and include various sensors to detect EEG, EKG, EOG, EMG, and tissue oxygen saturation. Biophysical sensors 110 may be placed at the surface of the nasal tube to allow further confirmation of OSA in the manner described in detail below. Because the biophysical sensors 110 may in some instances depend on contacting a cavity wall for signal detection, the position of one or more sensors may be adjusted relative to the surface of the device (e.g., by increasing or decreasing a sensor height) by deploying a balloon underneath the sensor to adjust the sensor position and thereby increase a sensor surface contact area. In this way, the signal sensitivity may also be increased for increased detection of ventilation patterns based on the acquired signal. Although balloons may be included to enhance a sensor surface contact in one instance, in another instance, one or more balloons may be included to anchor the device in place along with the nose stopper during the sleep study period. As such, pumping air into a balloon allows for increased contact between the balloon and nasal cavity, which thereby acts to anchor the device while preventing inward or outward movement of the device during the study. As such, placement of the device is stabilized, which advantageously allows for a more consistent imaging environment and enhanced clinical utility. Moreover, the seal between one or more balloons and the nasal cavity acts to create a tunnel through the device that directs the airflow therethrough. Therefore, airflow through the device may be optimized, which enables more sensitive diagnostic measurements during the sleep study.

As noted above, trachea sensors 112 may be included within second air sampling tube 220 that comprise one or more sensors for monitoring various conditions near the trachea below the point of constriction. For example, the trachea sensor may be a sound-detecting device comprising at least one of a microphone, stethoscope or Doppler device designed to detect one or more breathing patterns and anatomical changes associated with OSA. In an alternate embodiment, trachea sensors 112 may additionally or alternatively be included within the nasal tube and therefore detect breathing patterns and anatomical changes within nasal cavity 204. Although trachea sensor 112 is shown placed at the end of air sampling tube 220, this placement is non-limiting and the sensors may be located at any position along the device such that diagnostic measurements are enabled.

With respect to the devices shown in FIGS. 3A and 3B, collected sensor data may be relayed and processed by controller 120. Controller 120 may be a microcomputer, including microprocessor unit 122, input/output ports 330, an electronic storage medium for executable programs and calibration values shown as read only memory (ROM) chip 124 in this particular example, and a data bus. Storage medium read-only memory 124 can be programmed with computer readable data representing instructions executable by processor 122 for performing the methods described below as well as other variants that are anticipated but not specifically listed. Controller 120 may receive various signals from sensors coupled to an airway assessing apparatus, in addition to those previously discussed.

In addition to the sensors above, a head position sensor 108 may be embedded within nose stopper 210 for determining a head position during the sleep cycle. Nose stopper 210 may be located at the proximal end of the airway assessing apparatus and therefore prevent the device from sliding inward or outward during the sleep study period. As such, nose stopper 210 may have a larger diameter and a larger size compared to a nostril coupled to nasal cavity 204, which generally varies according to age, gender, and race. Placement of the device may be externally secured by adhering a piece of tape across the device to the patient's skin. Alternatively, in some examples, for example, FIG. 2A, the airway assessing apparatus may further include a distal balloon that is deployable to anchor the device and thereby prevent inward or outward movement relative to the cavity while also preventing accidental dislodge from sneezing or coughing. Although the shape of nose stopper 210 is shown cylindrical for simplicity, other shapes have been considered and are possible. In one example embodiment, head position sensor 108 is a three-axis accelerometer but this is non-limiting and the head position sensor may also be a gyroscope or sensor for detecting various motions therein. Since head position sensor 108 provides an indication of device orientation relative to a patient head position, the head position during the sleep cycle may be extracted from data collected by end imaging sensor 104 based on the relative orientation of airway assessing apparatus 102 with respect to the patient. Furthermore, since a head position during sleep can be time stamped, recorded and correlated to airway narrowing or collapse, the data may be used to determine a sleep position during the duration of the sleep cycle. For example, when a patient sleeps in a left lateral position at 90 degrees from the supine position (e.g., on their left side), said patient may experience 50% narrowing for 10 seconds at a frequency of three times/hr. Alternatively, in the supine position (e.g., asleep flat on their back facing upward), the same patient may experience 50% narrowing for 10 seconds at an increased frequency of 20 times/hr. As such, head position sensor 108 may be used for determining the head position during sleep and thereby to diagnose OSA from the data collected. In some embodiments, nose stopper 210 may include alignment mark 320 for aligning the airway assessing apparatus 102 relative to a head position at the outset of a sleep study. Therefore, the method according to the present disclosure allows for a positional AHI to be determined. For instance, because some people may snore more or experience an increased number of OSA episodes in a particular sleep position, an AHI based on the various sleep positions (e.g., left AHI, right AHI, or supine AHI) as well as the frequency of head movement, which are both factors in sleep quality, can be determined to further direct treatment.

Figure 4:
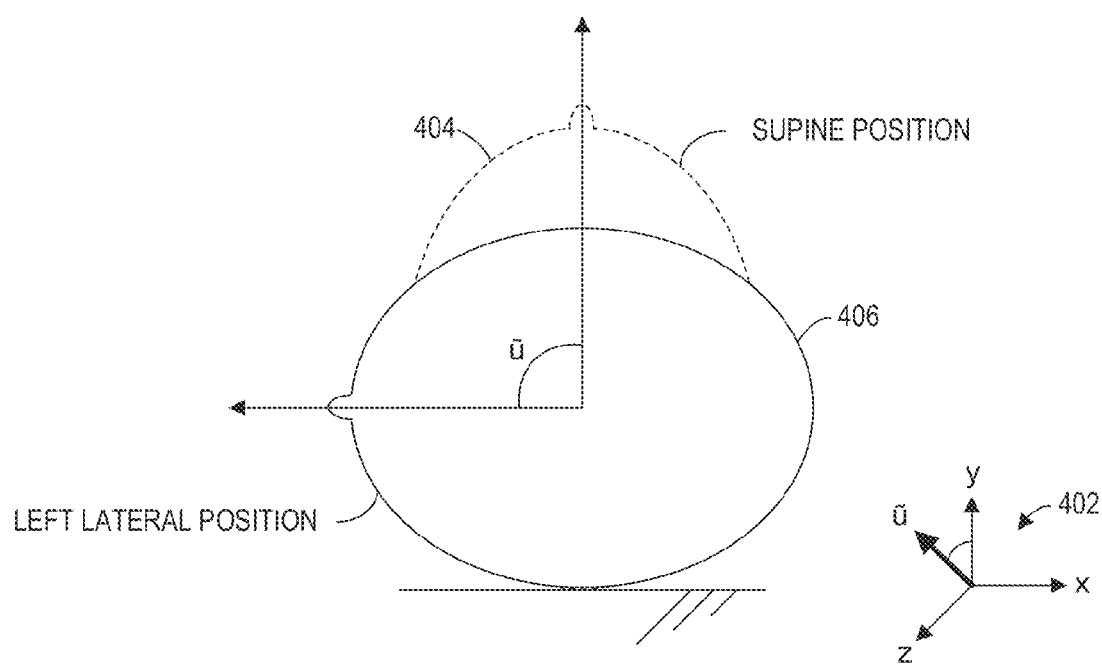
FIG. 4 schematically illustrates how the head position sensor may determine the head position based on data collected.

With respect to head position detection, FIG. 4 schematically illustrates how head position sensor 108 may differentiate between two head positions based on a relative sensor alignment compared to a fixed reference frame. Therein, Cartesian coordinate frame 402 (e.g., comprising x, y, and z axes) is generally shown along with a unit vector (û) oriented relative to the fixed coordinate frame. For example, in one embodiment, the y-axis of the Cartesian coordinate frame 402 may represent a gravitational field while û represents a vector associated with an accelerometer reference axis.

For illustrative purposes, FIG. 4 shows a schematic diagram of a sleep position from above a body axis, that is, looking down the longitudinal axis of the body from above. For example, at 404, the head position is in the supine sleep position with the body facing upward. Alternatively, at 406, the head is in a left lateral position (e.g., asleep on the left side). With such position data, the angle between the two identified sleep positions may be 90 degrees or another predetermined angle, which also corresponds to an angular displacement that can be measured by head position sensor 108. The two different sleep positions may produce different physiological sleep responses in the manner already described, which can also be detected by the methods described herein and used to diagnose OSA from the data collected. Although the angular displacement between supine position 404 and left lateral position 406 is shown as 90 degrees for simplicity, in general head position sensor 108 may detect any angular displacement and relative orientation (e.g., from movement in three dimensions instead of two dimensions).

Figure 5:
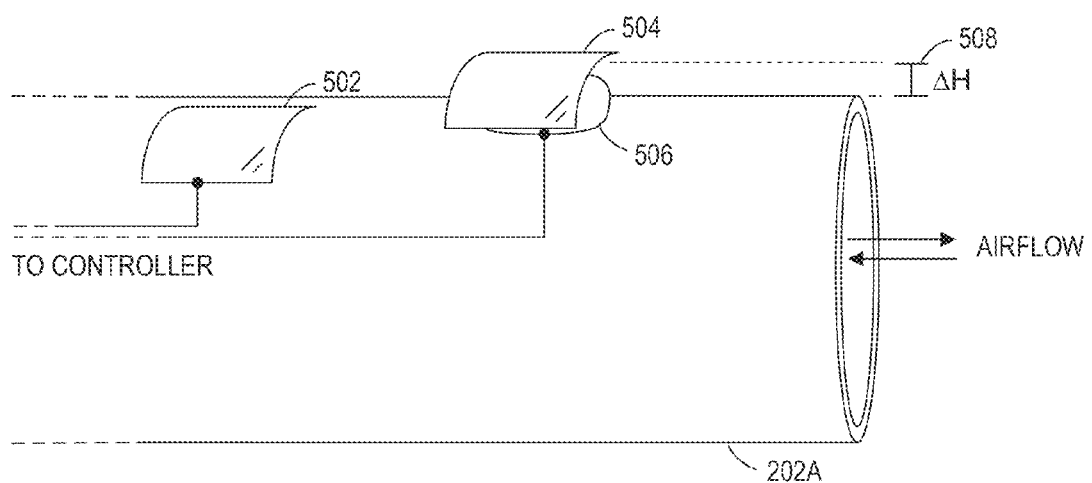
FIG. 5 shows an enlarged view of a hollow nasal imaging tube with exemplary adjustable sensors whose position changes via balloon deployment.

Turning now to FIG. 5, an enlarged view of nasal tube 202A is shown to further describe how a sensor position may be adjusted via balloon deployment. For illustrative purposes, two example contact-sensitive sensors are shown at 502 and 504. As described above, these sensors may represent EEG or EKG sensors that are located on the outside surface of nasal tube 202A. For simplicity, reference sensor 502 is shown flush with the tube surface whereas the position of adjustable sensor 504 is changed by deploying balloon 506 to adjust the position of the sensor via movement orthogonal to the tube surface. Connections between each sensor to controller 120 are shown schematically. With regard to inflation of the balloon, in one embodiment, a pilot balloon that includes an air injection port and valve may be included within the device for inflating one or more balloons therein. A sensor position may thus be adjusted by inflating a balloon located beneath the sensor in response to an output below a threshold in order to adjust the relative height 508 identified as ΔH to increase the surface contact area between the sensor and for instance, a wall of the nasal cavity. Although FIG. 5 shows a balloon that is used for changing the position of a sensor, one or more other balloons may alternatively or additionally be included for stabilizing the position of the device within the nasal cavity. Thereby, the airway assessing apparatus may be anchored into place to allow for enhanced observations during the sleep study. As noted above, one or more balloons may also seal or plug an airway so substantially all of the airflow is directed through the device. As such, the one or more balloons may stop air leaks around the tube and further create a tunneling effect that increases diagnostic accuracy and measurement sensitivity. Balloon inflation may therefore occur manually at the initial calibration stage in an awake patient, for instance, by a trained healthcare professional, or in some instances, by the patient who may also adjust the device position via rotation and/or further insertion and withdrawal. Although manual balloon inflation adjustments are described herein, in some embodiments, balloon pressure may be adjusted automatically based on a sensor detection level that falls below a pre-set or specified threshold.

Because the device and methods herein enable visual detection of OSA by observing airway obstructions from above the constriction point, FIGS. 6A-D show example illustrations of an airway obstruction in various degrees of closure during sleep. These examples are provided as illustrative examples and are not intended to be limiting in any way. In FIG. 6A, the open airway is shown surrounded by the pharynx and soft palate/uvula. The epiglottis is also shown and labeled accordingly. As described in detail above, as the tongue collapses, it moves in relation to the airway and thereby acts to constrict the flow of air therein. For example, in FIG. 6B, the airway is partially obstructed as the tongue (not visible) pushes against the soft palate and uvula (and epiglottis) in the manner already described with respect to FIGS. 1B and 1C. Then, in FIG. 6C, the tongue substantially fully collapses and thereby blocks the flow of air within the constricted airway. Finally, in FIG. 6D, as the tongue relaxes and slowly releases pressure within the oral cavity, the substantially blocked airway begins to subside in a manner that allows air to begin flowing again. As the obstruction subsides, the airway is thus re-established and the normal breathing pattern re-emerges during the sleep cycle. In this way, visual images of an airway closure episode can be collected and analyzed automatically along with other ancillary data to determine an obstruction or degree of obstruction throughout the sleep study period.

Figure 7:
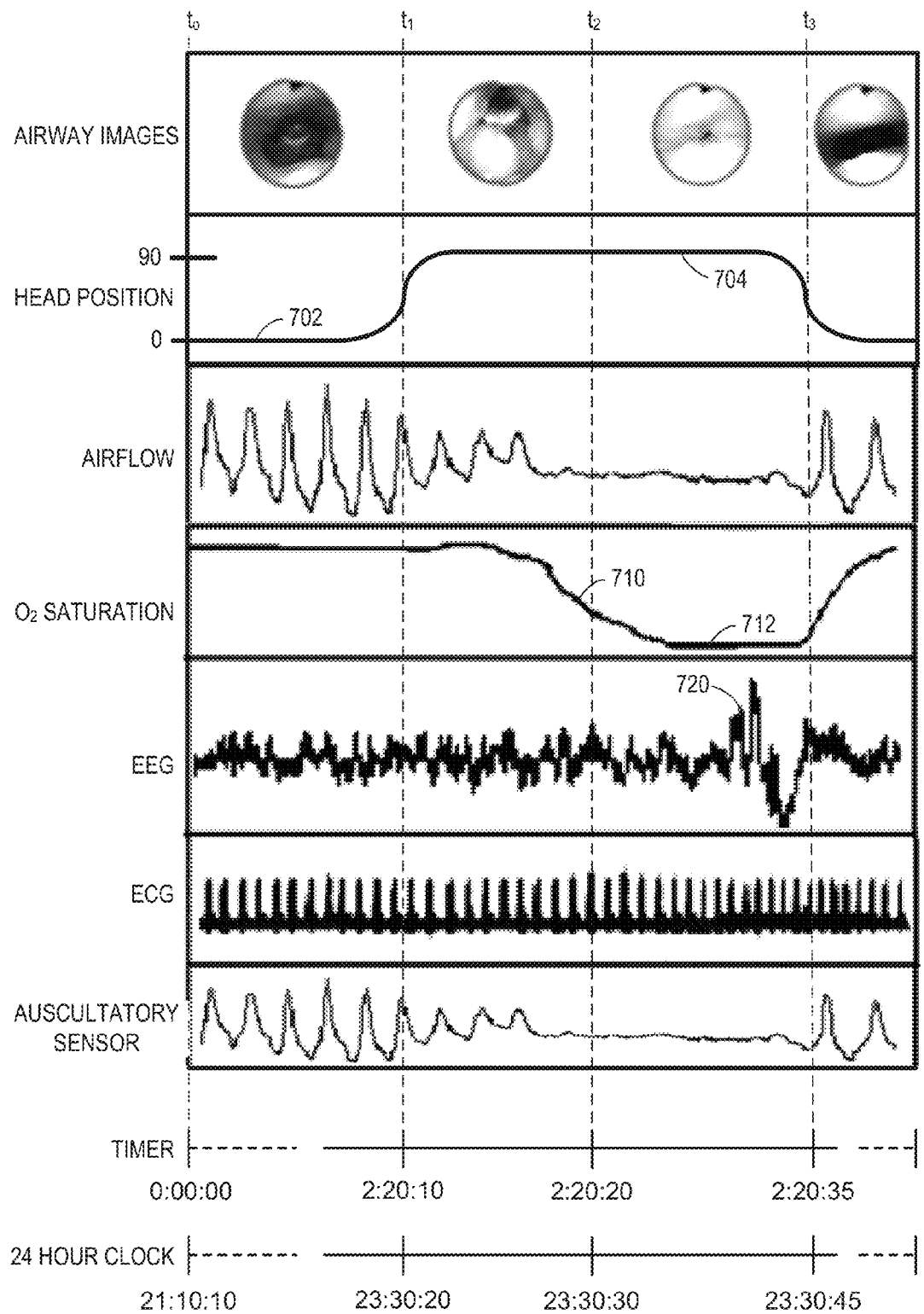
FIG. 7 is an example illustration showing how various data may be collected in combination with the visual images of FIG. 6 to diagnose sleep apnea.

Because airway assessing apparatus 102 comprises various additional sensors for monitoring and detection, the visual images collected may in some instances be correlated and/or confirmed by other physiological changes following an airway obstruction. For this reason, FIG. 7 shows an example illustration of various other data that may be collected in combination with the visual images shown in FIGS. 6A-D. Therein, various example sensor responses are also shown as a function of time where time increases from left to right. The degrees of obstruction or closure from FIGS. 6A-D are further identified by dashed vertical lines. For example, the first vertical line labeled $t_0$ signifies the start of the study. Then, as the study proceeds, onset of an airway constriction occurs at $t_1$ (e.g., clock time of 23:30:20 or timer setting of 2:20:10 whereas data collection began at 21:10:10) that signifies the airway being partially obstructed from collapse of the tongue. At $t_2$ (e.g., 23:30:30 or 2:20:20), the airway is substantially constricted and physiological responses begin to manifest due to a reduction in the amount of oxygen available. The constriction lasts until time point, $t_3$ (23:30:45 or 2:20:35), at which point the collapsed tongue is removed from the airway and therefore no longer blocks the airflow passage. In response to the removal of the constriction, the physiological conditions begin to return to their substantially normal levels as the body recovers from the airway obstruction. In response to the data collected, a healthcare professional or analytical program may analyze the data in order to identify an apnea episode (e.g., a closure that lasts 15 seconds) occurring when the patient sleeps in the supine position. In the example shown, the apnea episode is further accompanied by a cessation of airflow, severe oxygen desaturation, bradycardia and different brain waves compared to a reference curve (not shown) collected prior to the sleep study. Furthermore, although not shown explicitly in FIG. 7, data representing a count of the accumulated head movements may also be collected and used to identify the overall quality of sleep.

As shown in the example data of FIG. 7, visually observing an airway from above a point of constriction offers advantages compared to physiological and systemic changes that result from the airway constriction. For example, visual imaging data can identify an airway closure in real-time with substantially no lag time relative to the closure. In contrast, the data of FIG. 7 show that various additional data sensors may record a profile change after a timelag relative to the onset of constriction at $t_1$ and full constriction at $t_2$. As such, inclusion of these sensors provides confirmation of an OSA diagnosis based on the visual images. In addition, because sensed data patterns before $t_1$ are regular, implementation of analytical tools to detect subtle changes (e.g., reduction of amplitude or average value changes) and correlation of the results with visual images can be performed automatically in some instances. Furthermore, with the device according to the present disclosure, such analytical activities can occur remotely at one location while a sleep study is performed at another location.

With respect to the sensor data of FIG. 7, in the top plot, the airway images of FIGS. 6A-D are shown. Then, in the second plot, an example schematic of head position is provided. Such a pattern may be collected, for instance, by head position sensor 108. For simplicity, the angular data shown represent a head position relative to the left lateral position of FIG. 4. Therefore, 0 degrees at 702 occurs while the patient sleeps in the left lateral position, but an angle of 90 degrees shown at 704 occurs when the patient is asleep on their back in the supine position. It follows that an angle of 180 degrees may therefore occur when the patient sleeps in the right lateral position. For simplicity, in the example shown, a change in sleep position occurs along with the recorded episode of apnea. However, airway obstructions may occur for many reasons and the head position shown is provided simply for example.

The third plot in FIG. 7 shows an airflow pattern. Such a pattern may be collected, for instance, by airflow sensor 106 located within nasal tube 202B. Therein, prior to $t_1$, the airflow data undulate with larger amplitudes in response to inhalation and exhalation events during the breathing cycle. Then, between $t_1$ and $t_2$ when the patient changes sleeping position from left lateral to supine, an airway constriction occurs that produces a reduction in airflow. In response to the constriction, the amplitude of the undulating data begins to decrease, which signifies less airflow within the upper airway. At $t_2$, the amplitude is substantially zero due to the blocked airway. The duration of time between $t_2$ and $t_3$ may serve as a basis for assigning AHI and therefore diagnosing OSA.

In response to the blocked airway, the $O_2$ saturation, which is a relative measure of the amount of oxygen dissolved in a medium such as a body tissue may also provide a measure of airway closure. For example, in one embodiment, sensor 110 may measure $O_2$ saturation. However, this physiological response may exhibit a timelag compared to the onset of full blockage at $t_2$. For example, at 710, an $O_2$ sensor response may still be decreasing while the airflow response (and visual imaging) indicates a substantially full closure. Then, the oxygen saturation may decrease with a timelag to a lower plateau indicating closure at 712. The resulting timelag may lead to reduced sensitivities with respect to OSA diagnosis. For these reasons, the system and methods according to the present disclosure include such sensors for correlating the data patterns to the visual images obtained and further confirming a diagnosis. At $t_3$, once the blockage is removed, the oxygen levels begin to increase as the airflow is re-established within the upper airway.

In one embodiment, sensor 110 on the surface of the device may additionally or alternatively detect EEG or ECG within a cavity. However, in some instances, pattern changes (e.g., at 720) may be delayed relative to the occurrence of an airway closure, which may instead be used to support or establish the diagnosis according to the methods herein. In another embodiment, trachea sensor 112 may be an auscultatory sensor such as a microphone, stethoscope, or Doppler sound device for recording sounds within an airway associated with the heart or lungs and thereby provide a measure of arterial pressure. The blood pressure thereby increases in response to the airway closure and provides additional support for OSA diagnosis. In this way, a sound-detecting device may be used to indicate an airflow during the sleep cycle.

In view of the above, in one example embodiment, the device may collect visual images of an airway obstruction in combination with airflow information in relation to a head position during the sleep cycle. The data collected may be transmitted wirelessly or downloaded manually (e.g., via a wire inserted into a port) to a remote computing device and further analyzed to establish an OSA diagnosis. Furthermore, because the device includes a control system, sensor activation may be controlled remotely and one or more data patterns transmitted wirelessly for real-time analysis as the airway data is collected, which allows for expedient OSA diagnosis.

Figure 8:
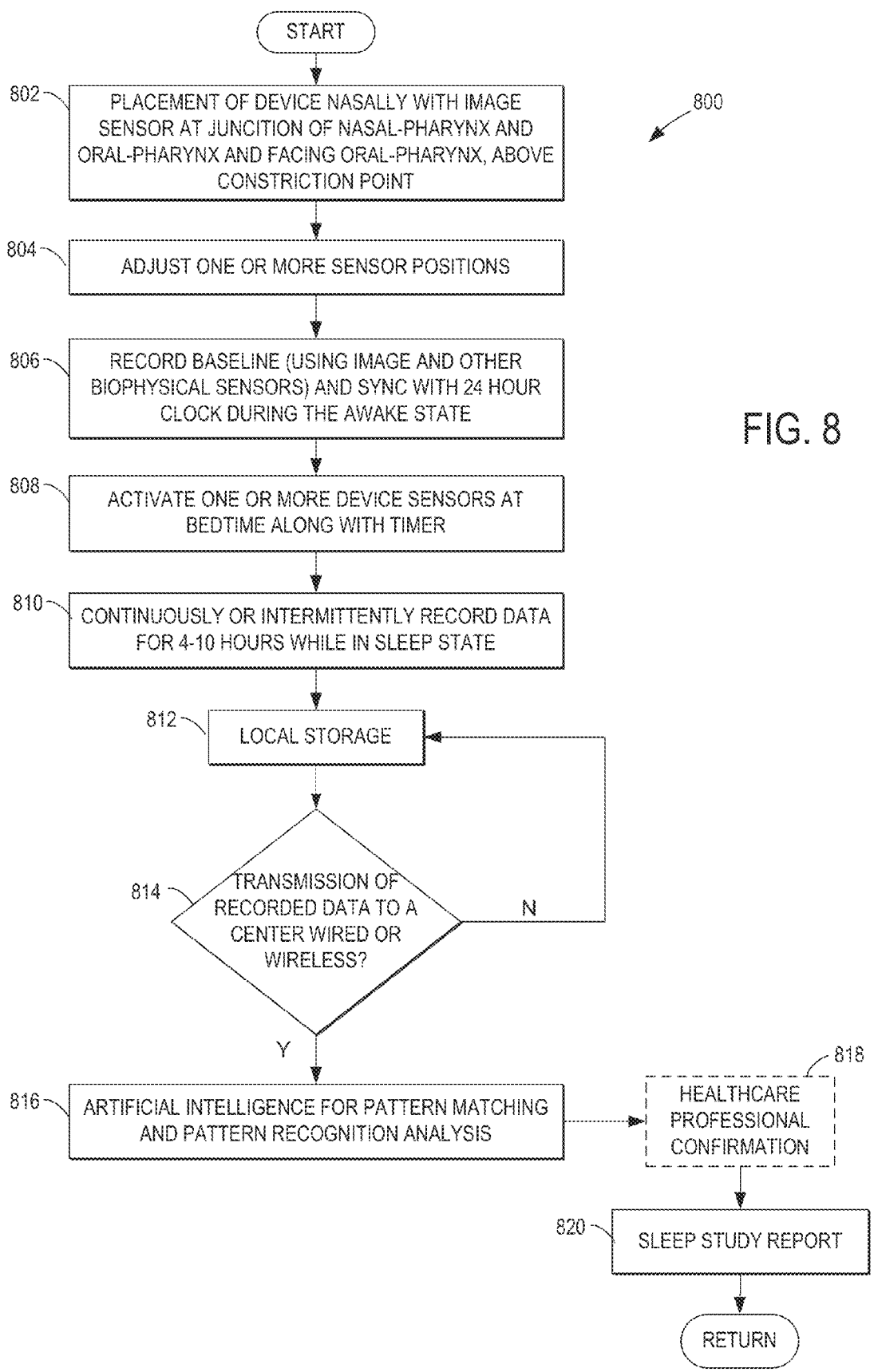
FIG. 8 is an example flow chart illustrating operation of the airway assessing apparatus according to the present disclosure.

FIG. 8 shows an example method by which airway assessing apparatus 102 may operate remotely. Specifically, FIG. 8 shows an example flow chart illustrating method 800 for controlling the device during a sleep study. As described already, the device may generate data in one location (e.g., in a home environment or sleep study center) while analysis occurs in a second location (e.g., at a doctor's office or in a second location within the sleep study center).

As described already, the method includes placement of an airway assessing apparatus in an upper airway with end imaging sensor 104 located above and in full view of a constriction point. For example, nasal tube 202B may be inserted into nasal cavity 204 until further insertion of the device is blocked by nose stopper 210. Then, because nasal tube 202B is curved relative to the longitudinal axis of the tube, end imaging sensor 104 may have a clear view of the oral cavity, including the nasopharynx, uvula and soft palate. Additionally, second air sampling tube 220 may be positioned in front of the oral cavity and thereby measure an airflow from the mouth.

At 804, method 800 includes adjusting one or more sensor positions to increase a surface contact area. For example, in one embodiment, a balloon may be inflated manually to adjust the position of a sensor (e.g., an EEG sensor) in a direction orthogonal to the tube surface based on a low but detectable signal that results from a low contact surface area. After adjustment of the one or more sensors, at 806 a baseline measurement of the imaging and biophysical sensors may be recorded during the awake state and synchronized with the 24-hour clock. Then, at 808, data collection by one or more sensors may commence at bed time along with the timer, which begins the sleep study. For example, in one embodiment, a timer including a start time and end time may be set within the device that controls the duration of the study. Furthermore, at 810, one or more sensors may be turned on and continuously or intermittently collecting data for the duration of the study, which is typically 4-10 hours in many cases. As one example, a study period may commence at 11:00 PM and proceed until 6:00 AM the next morning. Therefore, at 11:00 PM, nasopharyngeal light source 310 may be turned on while end imaging sensor 104 begins collecting data at a predetermined rate. Additional sensors, for example, airflow sensors 106 may also be activated at the start of the sleep study and therefore collect various data during the course of the study. The study may occur at home or in a sleep study center while a trained professional monitors the patient and/or data throughout the course of the study. Alternatively, to begin the study, the patient may push a start button on the device upon going to bed that activates one or more device sensors that continuously or intermittently record data for 4-10 hours while the patient is in the sleep state. In yet another alternative, a trained professional may remotely activate one or more sensors within the device after the patient has turned the airway assessing apparatus on.

At 812, the recorded data may be stored locally on the device until transmission for further analysis is requested. Therefore, 814 shows transmission of the data collected to a remote computing device. As noted above, the data may be transmitted to a location that is remote from the sleep study. If transmission is to occur during the study, then the data may be sent wirelessly via network 240 or manually downloaded via a wire for automatic pattern analysis on the remote computing device at 816. As one example, the remote computing device may include artificial intelligence for pattern matching and pattern recognition analysis while being configured to analyze one or more transmitted data sets. As such, a data set (e.g., images from end imaging sensor 104) can be compared to a reference database in order to identify various patterns associated with sleep apnea (e.g., cross-sectional area of the imaged airway). Thereby, computing device 130 may include programmable instructions for analyzing an image (e.g., by searching and processing area of the airway via the binary image code data) and further comparing the digital information to known stored patterns (e.g., images representing AHI ) or in some instances, by comparing to the baseline data collected when the subject is awake. Furthermore, because the data is time-stamped, the computing device may also analyze the data temporally to arrive at a determination of sleep apnea in the manner already described. In some embodiments, the data may be sent during the study but analysis may occur manually at the end of the study, for example, after being reviewed by a trained professional that identifies possible occurrences of airway patency. Alternatively, if transmission does not occur during the study, then the data may be stored locally on the device and downloaded at another time. At 818, collected data may be reviewed manually by a trained professional or automatically through a data processor located on the remote computing device. The data processor may comprise a pattern matching algorithm with pattern recognition capabilities to identify patterns of airway obstruction and a relationship to recorded airflows, oxygen saturations, and EEG or EKG changes. Upon conclusion of the study, at 820, a sleep study report may be generated by the remote computing device to facilitate physician diagnosis of OSA based on the data recorded.

Figure 9:
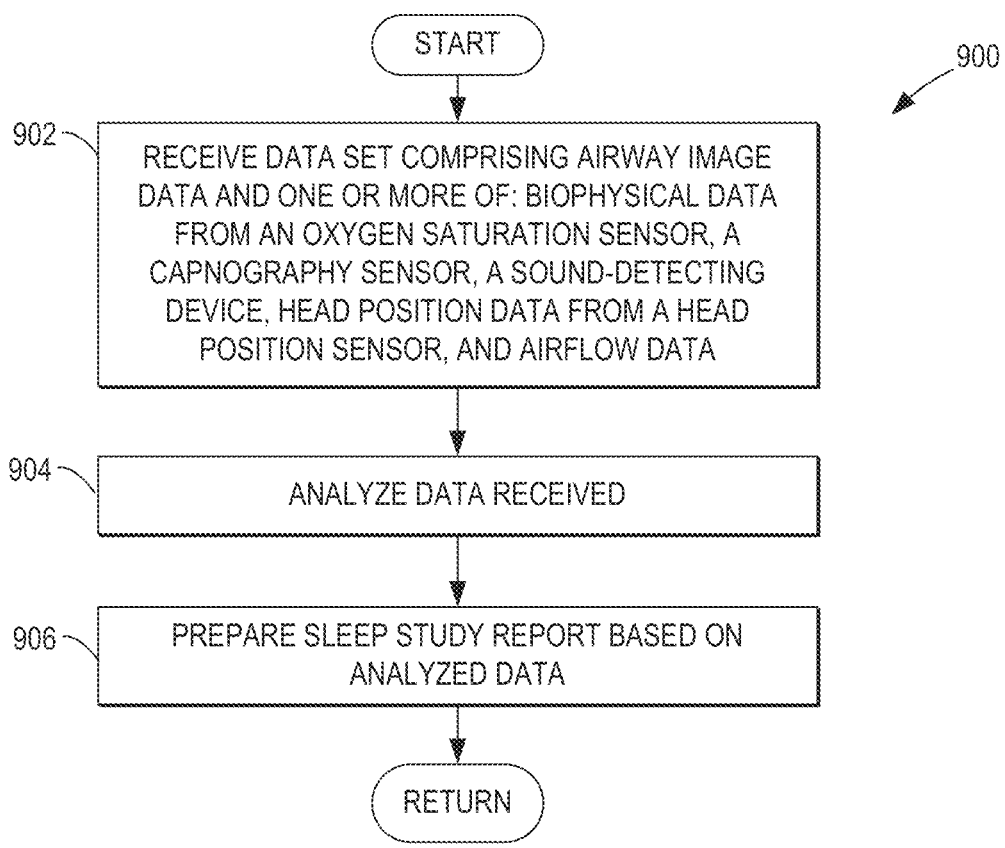
FIG. 9 is an example flow chart for diagnosing OSA based on data received from the airway assessing apparatus.

In FIG. 9, an example flow chart of method 900 illustrates a process for diagnosing OSA based on data received from the airway assessing apparatus. As described above, the wearable device may comprise an inflatable balloon to anchor the nasal tube such that the end imaging sensor is disposed in an airway image data collection position. As such, the method for monitoring an upper airway constriction associated with OSA includes receiving airway image data from a remote end imaging sensor coupled to a nasal tube disposed within an upper airway above a constriction point, where such airway image data was recorded during a sleep period, analyzing the data received, and further displaying the data and other pertinent information related to obstructive sleep apnea in a sleep study report. In this way, the airway image data can be used to identify airway closures related to obstructive sleep apnea.

At 902, method 900 includes receiving airway image data that is time-stamped from a remote end imaging sensor coupled to the nasal tube disposed within an upper airway above a constriction point, where such airway image data was recorded during a sleep period as described above. In one embodiment, method 900 includes receiving airway image data in combination with data from one or more additional sensors. For example, biophysical data may be collected from an oxygen saturation sensor and thereby represent an airway closure via a signal associated with an amount of dissolved oxygen in the body tissue. As another example, biophysical data may be additionally or alternatively collected from one or more capnography sensors capable of determining a gas level or exchange rate within an airway during the sleep period. As yet another example, data from a sound-detecting device (e.g., a microphone) may be collected that indicates an airway closure, and thereby an airflow. In another embodiment, method 900 may additionally or alternatively include receiving head position data from a sensor that indicates a head position relative to the nasal tube as described above with respect to FIG. 4. Although various examples are provided, it will be understood that a data set may be received that includes various combinations of the data collected by one or more sensors in combination with the visual images collected by the end imaging sensor. For instance, a data set received may include visual images along with head position data, which allows for a positional OSA to be determined in the manner described above. Alternatively, in another instance, visual images may be received in combination with a head position and/or an oxygen saturation level to determine the extent of OSA during a sleep cycle. Accordingly, data from all sensors present on the device may also be received and analyzed in the manner described herein.

At 904, method 900 further includes analyzing the airway image data to determine the frequency and number of airway obstructions that occur during a sleep study. For simplicity, the method is described with respect to the frequency and number of closures that occur. However, one or more remote devices may also be configured to analyze the extent of airway closure episodes and thereby determine AHI . As described above, AHI refers to the number of apnea and hypopnea episodes occurring within a time period, for instance, per hour of sleep, and the system described obtains the AHI via a direct imaging of the airway. Alternatively, OSA analytical toolbox 132 may include instructions for counting the number of head movements that occur during a sleep study and so include a counter indicating the number or frequency of head movements in order to determine the quality of sleep. Therefore, various analytical activities and combinations thereof may be performed to determine OSA, AHI , sleep quality, etc.

At 906, method 900 includes displaying in a sleep study report the airway image data to identify airway closures related to OSA. The sleep study report may include be a printout generated by a printing device (e.g., a printer) that relates to the sleep pattern data and OSA, however this is non-limiting and the sleep study report may also be a digital document that is viewed on a screen and/or securely transferred (e.g., via e-mail) to a healthcare professional, patient, etc. In this way, the device and methods described herein can be used to advantage for diagnosing obstructive sleep apnea, particularly in response to a sleep position, and especially when sleep activities occur remotely, by directly imaging the airway.

The reading of the description by those skilled in the art would bring to mind many alterations and modifications without departing from the spirit and the scope of the description. It is to be understood that the configurations and/or approaches described herein are exemplary in nature, and that these specific embodiments or examples are not to be considered in a limiting sense, because numerous variations are possible. The specific routines or methods described may represent one or more of any number of data collection strategies. As such, various acts illustrated may be performed in the sequence illustrated, in other sequences, in parallel, or in some cases omitted. Likewise, the order of the above-described processes may be changed.

It will be appreciated that the configurations and routines disclosed herein are exemplary in nature, and that these specific embodiments are not to be considered in a limiting sense, because numerous variations are possible. The subject matter of the present disclosure includes all novel and nonobvious combinations and subcombinations of the various systems and configurations, and other features, functions, and/or properties disclosed herein.

The following claims particularly point out certain combinations and sub-combinations regarded as novel and nonobvious. These claims may refer to "an" element or "a first" element or the equivalent thereof. Such claims should be understood to include incorporation of one or more such elements, neither requiring nor excluding two or more such elements. Other combinations and sub-combinations of the disclosed features, functions, elements, and/or properties may be claimed through amendment of the present claims or through presentation of new claims in this or a related application. Such claims, whether broader, narrower, equal, or different in scope to the original claims, also are regarded as included within the subject matter of the present disclosure.

The invention claimed:

1. A device for detecting airway obstructions during sleep to diagnose obstructive sleep apnea (OSA), comprising:
   a wearable hollow nasal tube having a first end and second end adapted to be positioned in an upper airway above a constriction point;
   an end imaging sensor at the first end of the nasal tube adapted to collect airway image data;
   a controller and communication interface configured to communicatively link and relay the airway image data to a select remote device to determine airway obstructions;
   a nose stopper connected to the second end of the nasal tube adapted to stabilize the nasal tube in a select position and direct air through the nasal tube, and
   an inflatable balloon on the nasal tube between the end imaging sensor and the nose stopper adapted to anchor the wearable nasal tube in the select position to collect the airway image data, wherein the inflatable balloon expands to a diameter greater than a diameter of the nasal tube.

2. The device of claim 1, wherein the nasal tube is curved relative to a longitudinal axis.

3. The device of claim 1, wherein the end imaging sensor is placed at a distal end of the nasal tube such that an image data collection position of the end imaging sensor is within a nasopharynx above the constriction point, and wherein the end imaging sensor is further angled downward relative to a nose opening to view an airway.

4. The device of claim 1, wherein the end imaging sensor is one of a camera and a thermal imaging device.

5. The device of claim 1, further comprising a light source to illuminate the airway for airway image data collection.

6. The device of claim 1, further comprising a sound-detecting sensor, wherein the sound-detecting sensor is at least one of a microphone, a stethoscope or a Doppler sound device.

7. The device of claim 1, further comprising an oxygen saturation sensor to collect airway data, where the airway data is relayed to a select remote device with the airway image data.

8. The device of claim 1, further comprising a head position sensor for collecting head position data relative to a device orientation, where the head position data is relayed to a select remote device with the airway image data.

9. The device of claim 8, wherein the head position sensor includes one of: an accelerometer, a gyroscope, and a sensor for detecting motion.

10. The device according to claim 6, further comprising a head movement counter to collect head position data including a number and frequency of head movements during sleep.

11. The device according to claim 1, further comprising one or more biophysical sensors comprising one or more of: an EEG sensor, an EKG sensor, and a capnography sensor capable of determining a gas level or exchange rate within an airway based on data collected.

12. The device of claim 1, wherein the nose stopper comprises mesh that enables air to pass through the device.

13. The device of claim 1, wherein the inflatable balloon is adapted to form a seal with a nasal cavity.

14. A system for remotely diagnosing obstructive sleep apnea, comprising:
 a tubular airway assessing apparatus adapted to be disposed within an upper airway, the tubular airway assessing apparatus comprising:
 a wearable nasal tube having a first end and second end with an end imaging sensor at the first end for directly viewing an airway to generate airway image data;
 a nose stopper at the second end adapted to stabilize the nasal tube in a select position and direct air flow through the first and second end of the nasal tube;
 an inflatable balloon on the nasal tube between the end imaging sensor and the nose stopper adapted to anchor the wearable nasal tube in the select position, wherein the inflatable balloon expands to a diameter greater than a diameter of the nasal tube;
 an airflow indicator configured to determine an airway airflow to generate airflow data;
 a processor, a communication interface and memory to collect and relay the airway image data and the airflow data over a network;
 a remote computing device configured to analyze breathing pattern data associated with obstructive sleep apnea;
 a communicative link between the tubular airway assessing apparatus and remote computing device configured to relay the airway image data to the remote computing device to determine airway obstructions.

15. The system of claim 14, wherein the airflow indicator is a sound-detecting sensor.

16. The system of claim 14, further comprising an oxygen tissue sensor.

17. The system of claim 14, further comprising a head position sensor and head movement counter to determine head position data during a sleep cycle.

18. The system of claim 14, further comprising one or more biophysical sensors comprising: an EEG sensor, an EKG sensor, and capnography sensor for determining a gas level or exchange rate within an airway based on data collected.

19. The system of claim 14, wherein the remote computing device is programmed to automatically analyze data received from the tubular airway assessing apparatus and where the airway image data is time-stamped.

20. The system of claim 14, wherein the tubular airway assessing apparatus further comprises an air sampling tube to sample air and airflow within a nasal cavity and/or an oral cavity.

21. The system of claim 20, wherein the air sampling tube is coupled to the nose stopper.

* * * * *